United States Patent [19]

Wild et al.

[11] Patent Number: 5,399,961
[45] Date of Patent: Mar. 21, 1995

[54] METHOD AND ARRANGEMENT FOR MONITORING THE PERFORMANCE LOSS OF AN OXYGEN PROBE

[75] Inventors: Ernst Wild, Oberriexingen; Helmut Denz, Stuttgart, both of Germany

[73] Assignee: Robert Bosch GmbH, Stuttgart, Germany

[21] Appl. No.: 981,383

[22] Filed: Nov. 25, 1992

[30] Foreign Application Priority Data

Nov. 30, 1991 [DE] Germany .......................... 41 39 561.1

[51] Int. Cl.$^6$ ............................................. G01N 27/00
[52] U.S. Cl. ...................................... 324/71.1; 123/688; 73/23.32
[58] Field of Search ....................... 324/71.1; 73/118.1, 73/1 G, 23.32; 123/688

[56] References Cited

U.S. PATENT DOCUMENTS

| | | | |
|---|---|---|---|
| 4,202,301 | 5/1980 | Early | 123/688 |
| 4,502,443 | 3/1985 | Hasegawa et al. | 123/688 |
| 4,505,246 | 3/1985 | Nakajima et al. | 73/23.32 |
| 4,677,955 | 7/1987 | Takao | 123/688 |
| 4,739,614 | 4/1988 | Katsuno et al. | 123/688 |
| 4,777,922 | 10/1988 | Mieno et al. | 123/688 |
| 5,052,361 | 10/1991 | Ono et al. | 73/23.32 |
| 5,058,556 | 10/1991 | Fukuma et al. | 123/688 |
| 5,065,728 | 11/1991 | Nakaniwa | 123/688 |
| 5,179,929 | 1/1993 | Miyashita et al. | 123/688 |
| 5,224,461 | 7/1993 | Nakaniwa | 123/688 |
| 5,243,954 | 9/1993 | Moss | 123/688 |
| 5,247,910 | 9/1993 | Abe | 123/688 |

FOREIGN PATENT DOCUMENTS 403272452 12/1991 Japan .......................... 73/23.32

*Primary Examiner*—Maura K. Regan
*Attorney, Agent, or Firm*—Walter Ottesen

[57] ABSTRACT

The invention relates to an arrangement for monitoring the performance loss of an oxygen probe arranged forward of a catalytic converter. The oxygen probe supplies an actual voltage U_ACT for a lambda controller for an internal combustion engine and the arrangement includes: a computation unit for computing the time-dependent mean value |U_ACT-U_DES| of the actual voltage U_ACT from a desired voltage U_DES; and, an evaluation unit for determining the performance loss of the oxygen probe on the basis of the time-dependent mean value. A simple method sequence which can be carried out with the above arrangement includes the step of deeming the probe to have an impermissibly high performance loss when the above-mentioned mean value drops below a threshold value. However, the quotient is preferably formed between the above-mentioned mean value and the mean value |FR_ACT-FR_DES| and the probe is deemed to have too great a performance loss when this quotient drops below a threshold value. The variable |FR_ACT-FR_DES| is the amount of the deviation of the output signal FR_ACT of the lambda controller from a desired value FR_DES. In this procedure, a very good signal/noise ratio is obtained which permits an especially reliable evaluation of the performance loss of the probe.

8 Claims, 2 Drawing Sheets

METHOD AND ARRANGEMENT FOR MONITORING THE PERFORMANCE LOSS OF AN OXYGEN PROBE

FIELD OF THE INVENTION

The invention relates to a method and an arrangement for monitoring the performance loss of an oxygen probe arranged forward of a catalytic converter. The oxygen probe supplies an actual voltage for a lambda controller for an internal combustion engine.

BACKGROUND OF THE INVENTION

The greater the loss in performance of an oxygen probe, the slower is the reaction thereof to changes in the oxygen content of the exhaust gas which flows around the probe. In this way, the period duration of the two-level control operation is increased which takes place with the aid of the probe signal. The controller output signal is generated with the aid of an integration process during the controller oscillations. For this reason, the amplitude of the controller oscillations also increase with an increase in the oscillation period. The probe is deemed to have a performance loss which is impermissibly great when the measured period duration exceeds a threshold value.

If probes are mounted forward and rearward of a catalytic converter for the lambda control, then the signal of the rearward probe, which always has a lower performance loss than the forward probe, is utilized to compensate for signal changes which are caused by the performance loss of the forward probe. When the compensation variable exceeds a threshold value, this shows that the forward probe has undergone a performance loss which is impermissible. The arrangement for the method just described utilizes the signal of a rearward probe wherein the loss of performance is low and operates with greater precision than the first-described arrangement which monitors the controller period duration. However, it is a disadvantage that the second, rearward probe is absolutely necessary.

SUMMARY OF THE INVENTION

It is an object of the invention to provide a method and an arrangement for monitoring the performance loss of an oxygen probe arranged forward of a catalytic converter which operate without the signal of a probe arranged rearward of the catalytic converter.

The method of the invention is for monitoring the performance loss of an oxygen probe arranged forward of a catalytic converter, the oxygen probe supplying an actual-value voltage $U\_ACT$ for a lambda controller of an internal combustion engine and the method includes the step of: monitoring the performance loss of the oxygen probe on the basis of a time-dependent mean value $|\overline{U\_ACT\text{-}U\_DES}|$ of the amount of the deviation $U\_ACT\text{-}U\_DES$ of the actual voltage $U\_ACT$ from a desired voltage $U\_DES$.

In the simplest embodiment, the monitoring takes place by means of a direct comparison of the above-mentioned mean value to a threshold value. The probe is deemed to have a performance loss which is impermissibly great as soon as there is a drop below this threshold. This procedure is based on the realization that a probe exhibits lower and lower voltage swings with increasing performance loss.

In an improved embodiment, the method of the invention is combined with the known method of monitoring period duration. More specifically, the quotient between the above-mentioned mean value and the mean value of the amount of the deviation of the output signal of the lambda controller is formed from a desired value and this quotient is compared to a threshold value. The probe is deemed to have an impermissibly great performance loss as soon as the quotient becomes less than the threshold value. This procedure leads to an especially good signal/noise ratio since the quotient becomes less when the above-mentioned voltage mean value becomes less and the quotient also becomes less when the controller-signal mean value in the denominator increases because of an increase of the period duration.

The mean value formation takes place advantageously either by means of a conventional software integration, by low-pass filtering or by making a count as to how often the deviation between the actual and desired values falls into a pregiven value range within a pregiven time duration. In the last case, the time duration can be pregiven in fixed time units or the time span can be defined by a pregiven number of oscillations. If the signals are scanned in fixed pregiven time intervals, then in the case of an averaged time span pregiven by the number of controller oscillations, the scannings must also be counted. Then, the ratio of the number of scanning values in the pregiven value range to the total number of scannings is the measure for the sought-after mean value.

During transient operations, the above-mentioned actual values deviate longer and, in part, also with greater intensity from the desired values corresponding to each actual value than in the case of steady-state operation of the lambda controlled internal combustion engine. The above-mentioned mean values then increase which, in the case of the voltage mean value, deceptively shows a better condition of the probe than is the actual condition; whereas, in the case of the mean value of the controller output signal, a poorer state is indicated than the actual state. In order to avoid these effects, it is advantageous to interrupt the mean value formation during transient operations of the internal combustion engine.

The arrangement of the invention is for monitoring the performance loss of an oxygen probe arranged forward of a catalytic converter, the oxygen probe supplying an actual voltage $U\_ACT$ for a lambda controller for an internal combustion engine and the arrangement includes: a computation unit for computing the time-dependent mean value $|\overline{U\_ACT\text{-}U\_DES}|$ of the actual voltage $U\_ACT$ from a desired voltage $U\_DES$; and, an evaluation unit for determining the performance loss of the oxygen probe on the basis of the time-dependent mean value.

The arrangement of the invention preferably includes an integration-stop device for interrupting the function of the computation device during transient operations of the lambda-controlled internal combustion engine. This integration-stop device prevents the possible faulty conclusions described above.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
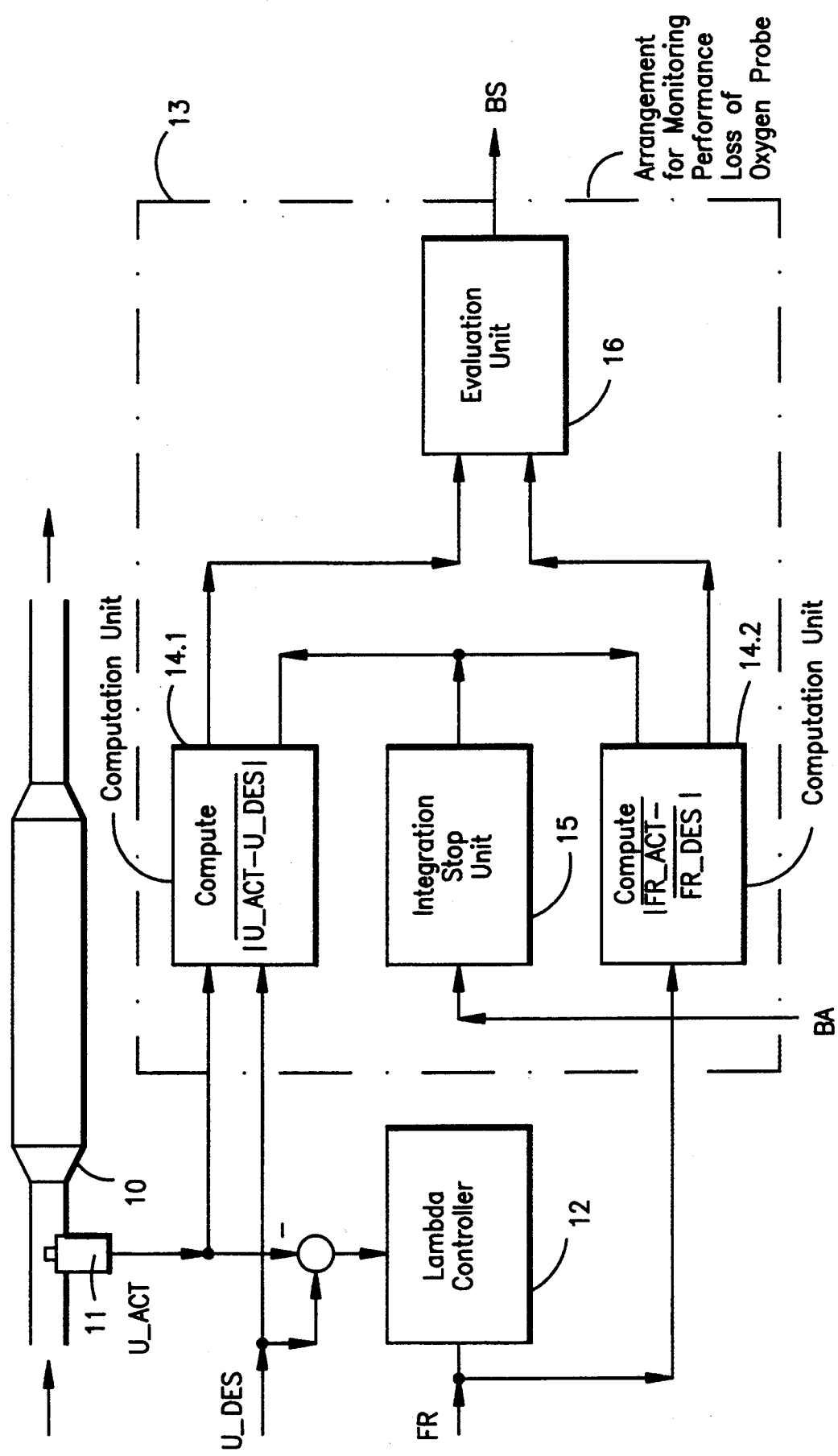
FIG. 1 is a schematic of a block diagram of an arrangement for monitoring the performance loss of an oxygen probe arranged forward of a catalytic converter; and, FIG. 2 shows a flowchart for explaining an embodiment of the method of the invention which can be carried out with the arrangement of FIG. 1.

FIG. 1 shows a catalytic converter 10 and an oxygen probe 11 arranged in the exhaust-gas channel leading to the catalytic converter. A lambda controller 12 and a monitoring device 13 are also provided. The following are contained within the monitoring device 13: a first computation unit 14.1, a second computation unit 14.2, an integration-stop unit 15 and an evaluation unit 16. The actual voltage U_ACT of the probe 11 is supplied to the lambda controller 12 and the first computation unit 14.1. The output signal FR of the lambda controller 12 is supplied to the second computation unit 14.2. The output signals of both computation units are supplied to the evaluation unit 16 which emits an evaluation signal BS which indicates whether or not the probe 1I has an impermissibly high performance loss. The computations in the two computation units 14.1 and 14.2 are interrupted in time durations in which the integration-stop unit 15 emits a corresponding signal. In order to ascertain when the computations should be interrupted, the integration-stop unit 15 receives an acceleration enrichment signal BA from a control unit (not shown), which influences the injection time of the fuel into the engine (not shown), to which the catalytic converter 10 is connected. This acceleration-enrichment signal indicates that the engine is just being transiently operated. Correspondingly, other signals of the engine control can be used which indicate transient operations. When the acceleration-enrichment signal or a similar signal is used directly, then this signal can be applied directly to each of the computation units 14.1 and 14.2. However, it is more advantageous to interpose the integration-stop unit 15. The integration-stop unit can interrupt the computations for a short time even after the decay of the acceleration-enrichment signal in order to ensure that the computations only resume when the engine is operating with certainty in the steady state.

The two computation units 14.1 and 14.2 each receive a desired value. The desired value U_DES preferably corresponds to a voltage assigned approximately to the lambda value 1. For a Nernst probe, these are typically approximately 450 mV. The desired value FR_DES as it is applied to the second computation unit 14.2 is preferably the value "1" when the lambda controller 12 emits a value FR which operates multiplicatively on the injection time. If, in contrast, the value FR acts additively, then the desired value is preferably the value "0".

Figure 2:
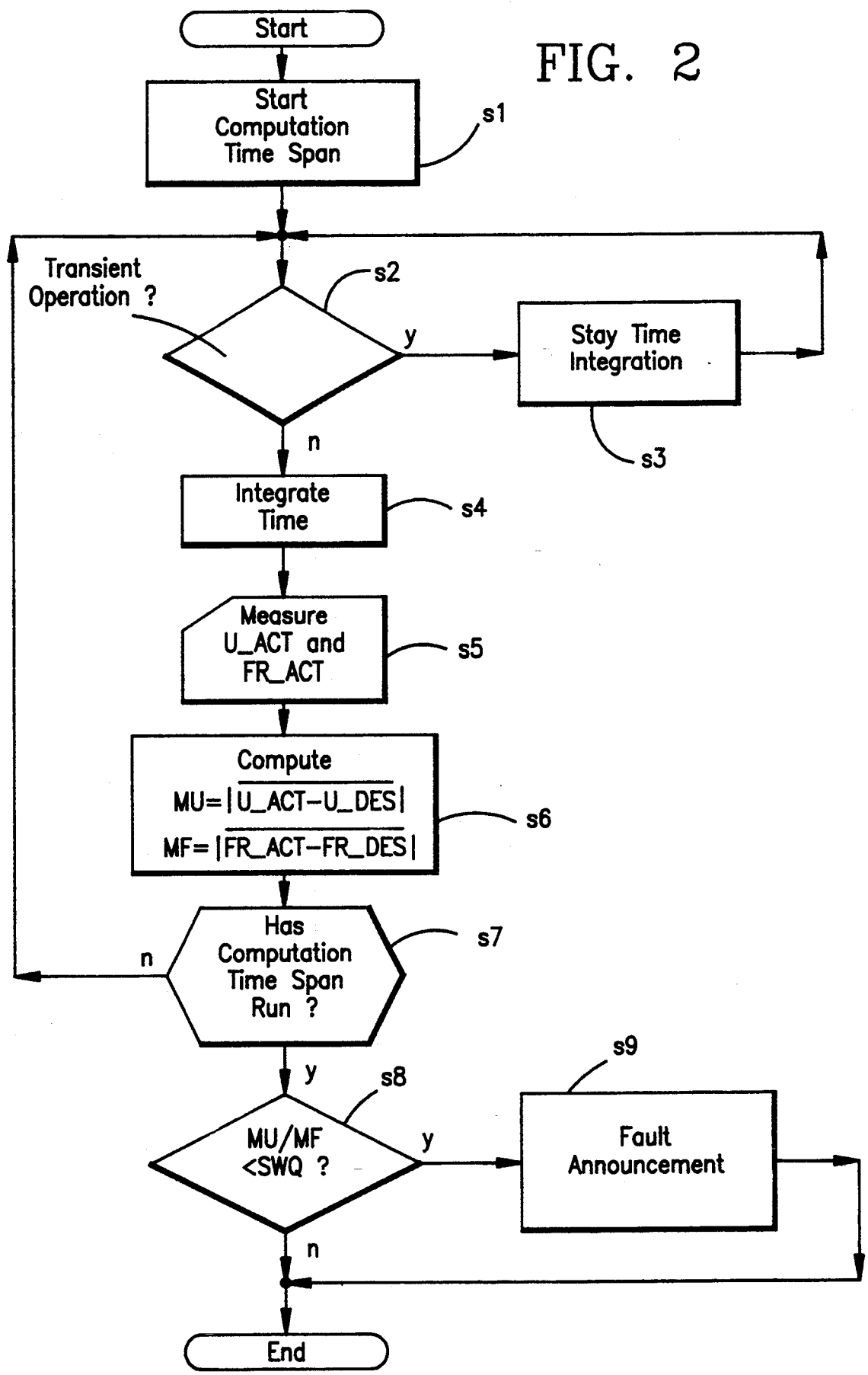

A method which can be carried out with the monitoring arrangement of FIG. 1 will now be explained with reference to the flowchart of FIG. 2.

After the start of the method, a computation time span is started in a step s1. Thereafter, the program enters a loop in which a check is first made in a step s2 by the integration-stop unit 15 as to whether the engine is operating transiently. If this is the case, then in a step s3, the time integration is interrupted and step s2 follows anew. Only when a determination is made in step s2 that no transient operation is present, then the integration of the computation time is continued in a step s4. The actual voltage U_ACT is then measured by the lambda probe 11 and the output signal FR_ACT is measured by the lambda controller 12 in a step s5. Mean values $\overline{|U\_ACT-U\_DES|}$ and $\overline{|FR\_ACT-FR\_DES|}$ are computed with these actual values and the above-mentioned desired values. The computation takes place, for example, in that first the above-mentioned differences between the particular actual and desired values are formed and the new difference is multiplied by a weighting factor (c) which is added to a previously obtained mean value multiplied by a different factor. This factor is (1−c). However, the computation can also take place by a counting of occurrences as described in the brief description of the invention above.

As soon as the computations of the mean values are concluded, a check is made in a step s7 as to whether the computation time span started in step s1 has run. If the pregiven computation time span has not yet run, then the above-mentioned loop is run through again starting with step s2. The loop is only left when it is determined in step s7 that the computation time span has run. In a step s8, the quotient between the mean values, which are computed in step s6 by the first and second computation units 14.1 and 14.2, is formed and the quotient is compared to a threshold value SWQ. The quotient formation and the comparison are carried out in the evaluation unit 16. If the comparison shows the quotient has dropped below the threshold value then the method is ended. The method is then again started only with the next operating cycle of the engine. The start of an operating cycle is defined in that the engine is started at a temperature below a threshold, for example, below 50° C.

If step 8 shows that there is drop below the threshold value SWQ, then this is an indication that the performance loss of the probe 11 is impermissibly great. A fault announcement then takes place in a step s9 which can comprise entering the fault into a fault memory and lighting a fault indicating lamp.

In the foregoing, the assumption was made that the voltage mean value is divided by the controller output mean value. However, the quotient formation can also take place inversely. Then, in step s8, a check is however not made as to whether there is a drop below a threshold; instead, a check is made if the threshold is exceeded. Furthermore, a method change in the context of a simplification is possible in that only the voltage mean value is computed by the computation unit 14.1 and the computation unit 14.2 is omitted. The evaluation unit 16 then checks only if the voltage mean value $\overline{|U\_ACT-U\_DES|}$ drops below a threshold SW.

It is understood that the foregoing description is that of the preferred embodiments of the invention and that various changes and modifications may be made thereto without departing from the spirit and scope of the invention as defined in the appended claims.

What is claimed is:

1. A method for monitoring the performance loss of an oxygen probe arranged forward of a catalytic converter, the oxygen probe supplying an actual-value voltage U_ACT for a lambda controller of an internal combustion engine, the method comprising the step of:

monitoring the performance loss of said oxygen probe by comparing a time-dependent mean value $\overline{|U\_ACT-U\_DES|}$ to a threshold value wherein U_ACT-U_DES defines the amount of deviation of the actual voltage U_ACT from a desired voltage U_DES.

2. The method of claim 1, comprising the further step of deeming said oxygen probe to have a performance loss which is impermissibly great when said mean value $|\overline{\text{U\_ACT-U\_DES}}|$ drops below said threshold value.

3. A method for monitoring the performance loss of an oxygen probe arranged forward of a catalytic converter, the oxygen probe supplying an actual-value voltage U\_ACT for a lambda controller of an internal combustion engine, the method comprising the steps of:

monitoring the performance loss of said oxygen probe on the basis of a time-dependent mean value $|\overline{\text{U\_ACT-U\_DES}}|$ which defines the amount of deviation of the actual voltage U\_ACT from a desired voltage U\_DES; and, deeming said oxygen probe to have a performance loss which is impermissibly great when the quotient $|\overline{\text{U\_ACT-U\_DES}}|/|\overline{\text{FR\_ACT-FR\_DES}}|$ drops below a threshold SWQ whereby the variable $|\overline{\text{FR\_ACT-FR\_DES}}|$ defines the amount of the deviation of the output signal FR\_ACT of the lambda controller from a desired value FR\_DES.

4. The method of claim 1, further comprising the step of forming the time-dependent mean value by integration.

5. The method of claim 1, further comprising the step of forming the time-dependent mean value by counting how often the deviation between the actual and desired values falls into a pregiven value range within a pregiven time span.

6. The method of claim 1, further comprising the step of interrupting the mean value formation during transient operation of the engine.

7. An arrangement for monitoring the performance loss of an oxygen probe arranged forward of a catalytic converter, the oxygen probe supplying an actual voltage U\_ACT for a lambda controller for an internal combustion engine, the arrangement comprising:

a computation unit for computing the time-dependent mean value $|\overline{\text{U\_ACT-U\_DES}}|$ of the actual voltage U\_ACT from a desired voltage U\_DES; and, an evaluation unit for determining the performance loss of the oxygen probe by comparing said time-dependent mean value to a threshold.

8. The arrangement of claim 7, further comprising an integration-stop unit for interrupting the operation of said computation unit during transient operations of the internal combustion engine.

* * * * *